Figure 1:
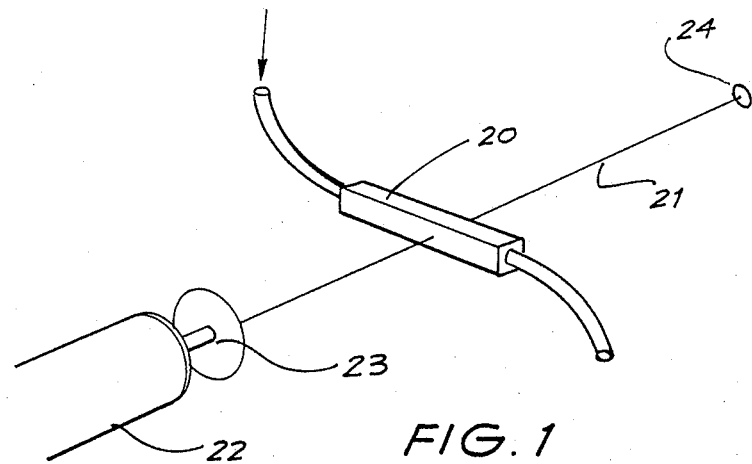

United States Patent [19]

Irvine

[11] Patent Number: 4,792,233

[45] Date of Patent: Dec. 20, 1988

[54] FLOW CELL FOR PARTICLE SCANNER

[75] Inventor: Philip A. Irvine, Round Corner, Australia

[73] Assignee: Commonwealth Scientific and Industrial Research Organisation, Campbell, Australia

[21] Appl. No.: 84,822

[22] PCT Filed: Sep. 5, 1986

[86] PCT No.: PCT/AU86/00263

§ 371 Date: May 27, 1987

§ 102(e) Date: May 27, 1987

[87] PCT Pub. No.: WO87/01451

PCT Pub. Date: Mar. 12, 1987

[30] Foreign Application Priority Data

Sep. 9, 1985 [AU] Australia .................... PH2344

[51] Int. Cl.[4] .................... G01N 21/05; G01N 15/02; G01N 15/10

[52] U.S. Cl. .................... 356/440; 356/246

[58] Field of Search .................... 356/246, 432, 440; 250/576

[56] References Cited

U.S. PATENT DOCUMENTS 3,728,032  4/1973  Noll .................... 356/246
4,056,324  11/1977  Gohde .................... 250/576

*Primary Examiner*—R. A. Rosenberger
*Attorney, Agent, or Firm*—Armstrong, Nikaido, Marmelstein & Kubovcik

[57] ABSTRACT

A flow cell for use in a fibre diameter measurement apparatus to obtain preferential alignment of the fibers in which fibers are caused to flow through a passage (14) the walls (16 and 16a) of which diverge in the direction of flow thereby causing forces to act on the fibres to rotate the ends of the fibres towards the diverging sides of the passage and thus rotate the fibers to a larger angle to the direction of flow.

3 Claims, 1 Drawing Sheet

FLOW CELL FOR PARTICLE SCANNER

The invention relates to an improved measurement cell for the measurement of the diameter of fibrous material by light scattering methods and in particular to the measurement of the diameter of fibre snippets, dispersed in a liquid, by light absorption in an apparatus known as the Fibre Diameter Analyser (FFDA or FDA). This apparatus is intended for measuring the diameter distribution of wool fibres or similar material and employs a measurement cell through which fibres are carried as a disperse suspension in a liquid flow.

Measurement cells used in apparatus for fibre diameter have used parallel sided, square cross-section conduits in the sensing zone.

In a publication by L. J. Lynch and N. A. Michie in the Textile Research Journal page 653, Vol. 46 No. 9, September 1976 the cell described was of square cross-section 2 mm by 2 mm.

In a previous publication by Lynch and Michie in Wool Technology and Sheep Breeding pages 22–27 Vol. XX No. 11, December 1973 a cell of 2 mm square is described with a means to electrostatically align fibres perpendicular to the flow of liquid through the cell.

In the prior art schemes the need for the fibre snippets to pass through the sensing zone at an angle to the direction of flow is recognized. In the case where no alignment mechanism is used this is not achieved since hydrodynamic forces tend to align fibres parallel to the flow direction.

When electrostatic fibre alignment is used a specially selected dispersing liquid must be employed to achieve a difference in dielectric constant between the fibres and the liquid. A high voltage must also be employed. These requirements are not practical for commercial applications.

In general the object of this invention is to produce an improved apparatus for the measurement of fibre diameter of snippets of textile fibres.

It is a further object of this invention to provide a means to obtain more favourable fibre orientation for measurement in the apparatus known as the FFDA or FDA.

It is also an object of this invention that as a result of this more favourable orientation that the measurement of a sample of fibre snippets should more closely correspond with measurement made on a similar sample of the same material by microscopic techniques.

It is also an object of this invention to increase the proportion of the fibre snippets which can be measured and to eliminate any difference in proportion between small and large diameter wool fibres.

Basically the above, as well as other objects, are obtained in accordance with this invention by causing the fibres, in suspension in a suitable dispersing liquid, to pass through a measurement cell with walls diverging in the dimension perpendicular to both that of the measurement beam and of the direction of flow. This divergence causes fibre snippets to take angles substantially different from that produced by hydrodynamic alignment in a parallel-sided cell.

Thus in this manner fibres will have an orientation such that measurement is favoured as they pass through the sensing beam.

The present invention consists in a flow cell having a body defining a passage through which a fiber-containing fluid can be caused to flow in a first direction. The body has two opposite walls defining sides of the passage, the walls being parallel to each other and transparent to radiation whereby fibers in the fluid can be illuminated and viewed by radiation travelling in a second direction through the walls and the fluid. Each of the walls lies in a first plane, the passage being further defined by a pair of opposite diverging flat surfaces each lying in a second plane, with the first planes being at right angles to the second planes. The second planes are parallel to the second direction of the radiation and are at an angle to the first direction of the fluid flow thereby forming a tapered passage having a first smaller end and second larger end, the passage having a width which increases uniformly and progressively from the first end to the second end. The passage has an inlet at the first end and an outlet at the second end, the flow of fluid in the tapered passage acting to produce a couple which rotates ends of the fibers towards the diverging flat surfaces of the passage and thus rotates the fibers to a larger angle to the direction of flow.

Figure 2:
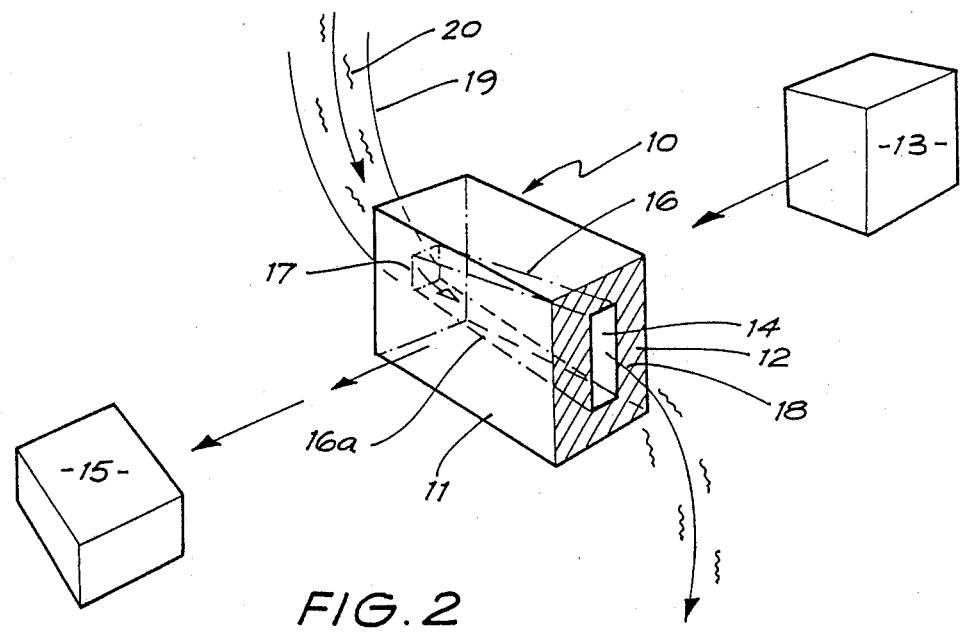

In order that the invention may be better understood and put into practice a preferred form of the invention is hereinafter described by way of example with reference to the accompanying drawings in which:

FIG. 1 is a schematic drawing of the sensing section of a fibre diameter measurement apparatus of the type incorporating this invention; and FIG. 2 is a schematic drawing showing the preferred form of the invention.

As seen in FIG. 1 the sensing area of a fibre diameter measurement apparatus of the FDA or FFDA type consists of a glass flow cell 20 through which flows a liquid carrying the fibre snippets to be measured in a very dilute suspension. Passing transversely through the cell is a narrow beam of light 21, circular in cross-section, from a helium-neon laser 22, which is aperture limited by a pinhole 23. As fibre snippets intersect this beam their diameter is sensed at a detector 24 by measuring the proportional reduction of light intensity of the beam representing the projected area of fibre within the beam and thus the average diameter within the beam. The photocell 24 comprises two semicircular cells which together form a full circle. The light intensity of the two halves separately is detected and compared during the passage of a fibre through the beam. A valid measurement is considered to have occurred only if the signals representing the change in light intensities at the two halves are identical at the moment that the signal representing the change in light intensity from the sum of the two halves is a maximum and also if the sum signal does not show multiple peaks. These conditions are easily satisfied if the fibre is at a large angle to the direction of flow and become less likely as the fibre becomes aligned with the flow direction as this decreases the probability that the image of fibre will pass symmetrically across the two halves of the photocell. If a fibre is curved along its length it can be seen that it will have an increased probability of acceptance than one which is straight. Since the probability of curvature in a wool fibre is larger in smaller diameter fibres it can be seen that a bias can occur toward the acceptance of these thinner fibres. The arrangement described thus far is that used in the commercial manufacture of an instrument for measurement of fibre diameter and is well known.

As described above the fibre snippets are required to intersect the beam such that a measurement of the projected area within the beam may be made. This invention provides a means to align the fibre snippets at a sufficient angle to the flow direction as to greatly increase the probability of this occurrence compared with that for fibres aligned by the hydrodynamic forces in a parallel-sided cell. The invention provides a measurement flowcell which may substitute for the parallel-sided cell in the existing apparatus or which may be used in other similar apparatus for fibre diameter measurement.

The measurment cell consists of a body composed of glass or other transparent material defining a passage through which the particle-containing liquid is passed, at least two opposite walls being transparent, parallel and highly polished and through which the sensing light beam passes, two opposite walls being at an angle to the flow direction forming a tapered channel with an included angle between 6 degrees and 60 degrees with the smaller end forming the inlet and the larger the outlet for the liquid flow.

As fibres are transported by the liquid through the expanding section of the cell they are subject to forces which alter the orientation of the fibre.

The preferred form of the invention is described with reference to FIG. 2. The cell 10 has parallel sidewalls 11 and 12 which are transparent to light from a laser source 13. This light passes through the passage 14 to a detector 15. The passage has tapering sides 16 and 16a which diverge with an included angle between 6 degrees and 60 degrees from the smaller entry in 17 of the cell to the larger exit 18. A flow of liquid passes down the inlet tube 19 and passes through the cell carrying with it the fibre snippets 20.

Fibre snippets are suspended in a carrier liquid which, for wool, is preferably iso-propanol containing a proportion of water, generally selected to be approximately 8% by volume.

The snippet suspension is allowed to flow from a mixing bowl through a parallel sided inlet tube towards the cell. Flow in the inlet tube is laminar and the hydrodynamic forces cause the fibre snippets to align with their major axes near to the direction of flow.

When the fibre snippets enter the expanding area of the cell they are subject to a force which tends to move the ends of the fibre towards the expanding faces of the cell. This force arises from separation of the flow from the walls and the resulting turbulence.

The cell shown in FIG. 2 must be constructed to allow unobstructed passage of the optical sensing beam. The sides of the cell through which the beam passes must be flat, parallel and highly polished and constructed of transparent material. The other internal and external faces of the cell must be smooth but need not be polished. The preferred spacing between the parallel internal faces is 2 mm and the preferred internal included angle between the diverging faces is 16 degrees although other angles also produce a change in orientation.

I claim:

1. A flow cell having a body defining a passage through which a fiber-containing fluid can be caused to flow in a first direction, said body having two opposite walls defining sides of said passage, said walls being parallel to each other and transparent to radiation whereby fibers in said fluid can be illuminated and viewed by radiation travelling in a second direction through said walls and said fluid, each of said walls lying in a first plane, said passage being further defined by a pair of opposite diverging flat surfaces each lying in a second plane, said first planes being at right angles to said second planes, said second planes being parallel to said second direction of said radiation and being at an angle to said first direction of said fluid flow thereby forming a tapered passage having a first smaller end and a second larger end, said passage having a width which increases uniformly and progressively from said first end to said second end, said passage having an inlet at said first end and an outlet at said second end, said flow of fluid in said tapered passage acting to produce a couple which rotates ends of said fibers towards said diverging flat surfaces of said passage and thus rotates said fibers to a larger angle to said direction of flow.

2. A flow cell as claimed in claim 1, wherein said opposite diverging surfaces of said tapered channel having an angle between them of between 6 degrees and 60 degrees.

3. A flow cell as claimed in claim 2, wherein said angle between said opposite diverging surfaces is 16 degrees

* * * * *